United States Patent
Kiyose et al.

(10) Patent No.: US 9,868,137 B2
(45) Date of Patent: Jan. 16, 2018

(54) ULTRASONIC TRANSDUCER DEVICE, PROBE, ELECTRONIC INSTRUMENT, AND ULTRASONIC DIAGNOSTIC DEVICE

(71) Applicant: SEIKO EPSON CORPORATION, Tokyo (JP)

(72) Inventors: Kanechika Kiyose, Nagano (JP); Hironori Suzuki, Nagano (JP); Hiroshi Matsuda, Gifu (JP)

(73) Assignee: Seiko Epson Corporation, Tokyo (JP)

(*) Notice: Subject to any disclaimer, the term of this patent is extended or adjusted under 35 U.S.C. 154(b) by 896 days.

(21) Appl. No.: 14/227,508

(22) Filed: Mar. 27, 2014

(65) Prior Publication Data

US 2014/0296715 A1    Oct. 2, 2014

(30) Foreign Application Priority Data

Mar. 29, 2013  (JP) ................................ 2013-071581
Mar. 20, 2014  (JP) ................................ 2014-058149

(51) Int. Cl.
- *B06B 1/06* (2006.01)
- *A61B 8/00* (2006.01)
- *G01N 29/44* (2006.01)

(52) U.S. Cl.
CPC .......... *B06B 1/0622* (2013.01); *A61B 8/4483* (2013.01); *B06B 1/0611* (2013.01); *G01N 29/44* (2013.01)

(58) Field of Classification Search
CPC ... B06B 1/0603; B06B 1/0607; B06B 1/0622; B06B 1/0629; H01L 41/053

(Continued)

(56) References Cited

U.S. PATENT DOCUMENTS

2006/0176343 A1   8/2006  Shimada et al.
2006/0238067 A1*  10/2006  Dausch ................ A61B 8/4483
                                            310/311

(Continued)

FOREIGN PATENT DOCUMENTS

JP   2005-051688 A   2/2005
JP   2006-198996 A   8/2006

(Continued)

OTHER PUBLICATIONS

Duval, F.F.C. et al.; "Fabrication of PZT Composite Thick Films for High Frequency Membrane Resonators"; Journal of Electroceramics, vol. 13, No. 1-3; Jul. 1, 2004; pp. 267-270.

(Continued)

*Primary Examiner* — Derek Rosenau
(74) *Attorney, Agent, or Firm* — Global IP Counselors, LLP

(57) ABSTRACT

An ultrasonic transducer device includes a base, a plurality of piezoelectric elements, a conductive body and an insulating film. The base has a plurality of vibrating film portions arranged in an array pattern. The piezoelectric elements are respectively disposed on the vibrating film portions. The conductive body is disposed on the base, and arranged inside and outside of an area corresponding to each of the vibrating film portions in a plan view as viewed along a thickness direction of the base. The insulating film is disposed on the conductive body only at outside of the area corresponding to each of the vibrating film portions in the plan view.

20 Claims, 9 Drawing Sheets

(58) Field of Classification Search
USPC .................................. 310/322, 334, 335, 340
See application file for complete search history.

(56) References Cited

U.S. PATENT DOCUMENTS

| | | |
|---|---|---|
| 2006/0290747 A1 | 12/2006 | Shimada et al. |
| 2013/0066209 A1 | 3/2013 | Matsuda |
| 2014/0219063 A1* | 8/2014 | Hajati .................. B06B 1/0292 367/157 |
| 2016/0121368 A1* | 5/2016 | Nakamura .......... H01L 41/0825 600/459 |

FOREIGN PATENT DOCUMENTS

| | | |
|---|---|---|
| JP | 2006-231909 A | 9/2006 |
| JP | 2007-175989 A | 7/2007 |
| JP | 2010-042683 A | 2/2010 |
| WO | 2005/028207 A1 | 3/2005 |

OTHER PUBLICATIONS

Wang, Zhihong et al.; "Micromachined ultrasonic transducers and arrays based on piezoelectric thick film"; Applied Physics A; Materials Science & Processing, vol. 91, No. 1; Jan. 25, 2008; pp. 107-117.
The Extended European Search Report for the corresponding European Application No. 14162335.5 dated Dec. 11, 2015.

* cited by examiner

ULTRASONIC TRANSDUCER DEVICE, PROBE, ELECTRONIC INSTRUMENT, AND ULTRASONIC DIAGNOSTIC DEVICE

CROSS-REFERENCE TO RELATED APPLICATIONS

This application claims priority to Japanese Patent Application Nos. 2013-071581 filed on Mar. 29, 2013 and 2014-058149 filed on Mar. 20, 2014. The entire disclosure of Japanese Patent Application Nos. 2013-071581 and 2014-058149 is hereby incorporated herein by reference.

BACKGROUND

Technical Field

The present invention relates to an ultrasonic device as well as a probe, electronic instrument, ultrasonic image device and the like that uses that.

Related Art

Ultrasonic transducer devices are generally known. For example, with the ultrasonic transducer device noted in Japanese Unexamined Patent Publication No. 2005-51688, a plurality of vibrating films are provided in an array pattern. A piezoelectric element is formed on the vibrating film. The piezoelectric element is covered by a protective film. The protective film expands with an even thickness on the inside area and the outside area of the vibrating film.

SUMMARY

The ultrasonic waves act on the vibrating film. The ultrasonic waves cause ultrasonic vibration of the vibrating film. Current is output from the piezoelectric element according to the ultrasonic vibration of the vibrating film. In this way, the ultrasonic transducer device detects ultrasonic waves. At this time, when the protective film expands uniformly with an even thickness continuously on the inside area and the outside area of the vibrating film, the flexibility of the vibrating film is reduced. The detection sensitivity of the ultrasonic waves decreases.

According to at least one aspect of the present invention, it is possible to provide an ultrasonic transducer device that realizes protection of a conductive body while maintaining good flexibility of the vibrating film.

An ultrasonic transducer device according to one aspect includes a base, a plurality of piezoelectric elements, a conductive body, a first insulating film and a second insulating film. The base has a plurality of vibrating film portions arranged in an array pattern. The piezoelectric elements are respectively disposed on the vibrating film portions. The conductive body is disposed on the base, and arranged inside and outside of an area corresponding to each of the vibrating film portions in a plan view as viewed along a thickness direction of the base. The first insulating film is disposed on the conductive body only at outside of the area corresponding to each of the vibrating film portions in the plan view. The second insulating film having a film thickness smaller than a film thickness of the first insulating film, and disposed at least partially on each of the piezoelectric elements and only at inside of the area corresponding to each of the vibrating film portions in the plan view.

Ultrasonic waves act on the vibrating film. Ultrasonic waves cause ultrasonic vibration of the vibrating film. Current is output from the piezoelectric element according to the ultrasonic vibration of the vibrating film. In this way, the ultrasonic transducer device detects ultrasonic waves. Here, the first insulating film protects the conductive body. Since the first insulating film does not affect the vibrating film, good flexibility of the vibrating film is maintained.

The ultrasonic transducer device as described above preferably further includes a third insulating film having a film thickness smaller than the film thickness of the second insulating film, and connected to the first insulating film and the second insulating film. In this way, the conductive body can be even more reliably protected. The third insulating film is thinner than the first and second insulating films, so it is possible to maintain the vibrating film vibration operation well.

In the ultrasonic transducer device as described above, each of the piezoelectric elements preferably includes a first electrode disposed on the vibrating film portion, a piezoelectric film covering at least a portion of the first electrode, and a second electrode covering at least a portion of the piezoelectric film. The conductive body preferably includes a first conductive body part connected to the first electrode of each of the piezoelectric elements, and a second conductive body part connected to the second electrode of each of the piezoelectric elements. And the ultrasonic transducer device preferably further includes a fourth insulating film covering a portion of the piezoelectric film that is not covered by the second electrode or the second conductive body part.

In the ultrasonic transducer device as described above, the fourth insulating film preferably includes two sections that sandwich the second electrode from both sides of the second electrode.

In the ultrasonic transducer device as described above, the piezoelectric film preferably covers at least a portion of the first electrode and a portion of a corresponding one of the vibrating film portions, and the second insulating film preferably has a first film body part disposed on the second electrode and having a first film thickness, and a second film body part covering the piezoelectric film on side surfaces of the piezoelectric element and having a second film thickness greater than the first film thickness.

In the ultrasonic transducer device as described above, the piezoelectric film is preferably layered on the first electrode, and separated from a surface of a corresponding one of the vibrating film portions by the first electrode, the second electrode is preferably layered on the piezoelectric film, and separated from the first electrode by the piezoelectric film, and the second insulating film preferably has a first film body part disposed on the second electrode and having a first film thickness, and a second film body part covering the second electrode, the piezoelectric film, and the first electrode on side surfaces of the piezoelectric element and having a second film thickness greater than the first film thickness.

An ultrasonic transducer device according to another aspect includes a base, a plurality of piezoelectric elements, a conductive body, and an insulating film. The base has a plurality of vibrating film portions arranged in an array pattern, each of the vibrating film portions having a rectangular shape defined by a pair of long sides and a pair of short sides in a plan view as viewed along a thickness direction of the base. The piezoelectric elements are respectively disposed on the vibrating film portions. The conductive body is disposed on the base, and arranged inside and outside of an area corresponding to each of the vibrating film portions in the plan view. The insulating film covers outside of the area corresponding to each of the vibrating film portions and only a portion of each of the long sides of the vibrating film portions in the plan view.

In the ultrasonic transducer device as described above, the insulating film preferably covers each of the short sides of the vibrating film portions in the plan view.

In the ultrasonic transducer device as described above, each of the piezoelectric elements preferably includes a first electrode disposed on the vibrating film portion, a piezoelectric film covering at least a portion of the first electrode, and a second electrode covering at least a portion of the piezoelectric film. The conductive body preferably includes a first conductive body part connected to the first electrode of each of the piezoelectric elements, and a second conductive body part connected to the second electrode of each of the piezoelectric elements. The second insulating film preferably covers a portion of the piezoelectric film that is not covered by the second electrode or the second conductive body part.

In the ultrasonic transducer device as described above, the insulating film is preferably arranged at both sides of the second electrode so as to sandwich the second electrode.

An ultrasonic transducer device according to another aspect includes a base, a plurality of piezoelectric elements, a conductive body, and an insulating film. The base has a plurality of vibrating film portions arranged in an array pattern. The piezoelectric elements are respectively disposed on the vibrating film portions. The conductive body is disposed on the base, and arranged inside and outside of an area corresponding to each of the vibrating film portions in a plan view as viewed along a thickness direction of the base. The insulating film is disposed on the conductive body only at outside of the area corresponding to each of the vibrating film portions in the plan view.

The ultrasonic waves act on the vibrating film. The ultrasonic waves cause ultrasonic vibration of the vibrating film. Current is output from the piezoelectric element according to the ultrasonic vibration of the vibrating film. In this way, the ultrasonic transducer device detects ultrasonic waves. Here, the insulating film protects the conductive body. The insulating film does not affect the vibrating film, so flexibility of the vibrating film is maintained well. Therefore, it is possible to maintain the ultrasonic wave detection sensitivity.

It is possible to use any of the ultrasonic transducer devices incorporated in a probe. The probe can be equipped with the ultrasonic transducer device and a case supporting the ultrasonic transducer device.

The ultrasonic transducer device can be used incorporated in an electronic instrument. The electronic instrument can be equipped with the ultrasonic transducer device, and a processing unit connected to the ultrasonic transducer device, configured to process output signals of the ultrasonic transducer device.

The ultrasonic transducer device can be used incorporated in an ultrasonic image device. The ultrasonic image device can be equipped with the ultrasonic transducer device, a processing unit connected to the ultrasonic transducer device and configured to process output signals of the ultrasonic transducer device and generate an image, and a display device configured to display the image.

BRIEF DESCRIPTION OF THE DRAWINGS

Referring now to the attached drawings which form a part of this original disclosure.

DETAILED DESCRIPTION OF EXEMPLARY EMBODIMENTS

Following, embodiments of the present invention will be explained with reference to the attached drawings. The embodiments explained below shall not be construed as unreasonably limiting the subject matter of the present invention described in the claims, and all the elements explained in the embodiments are not necessarily essential to the solving means of the present invention.

(1) Overall Configuration of Ultrasonic Diagnostic Device

Figure 1:
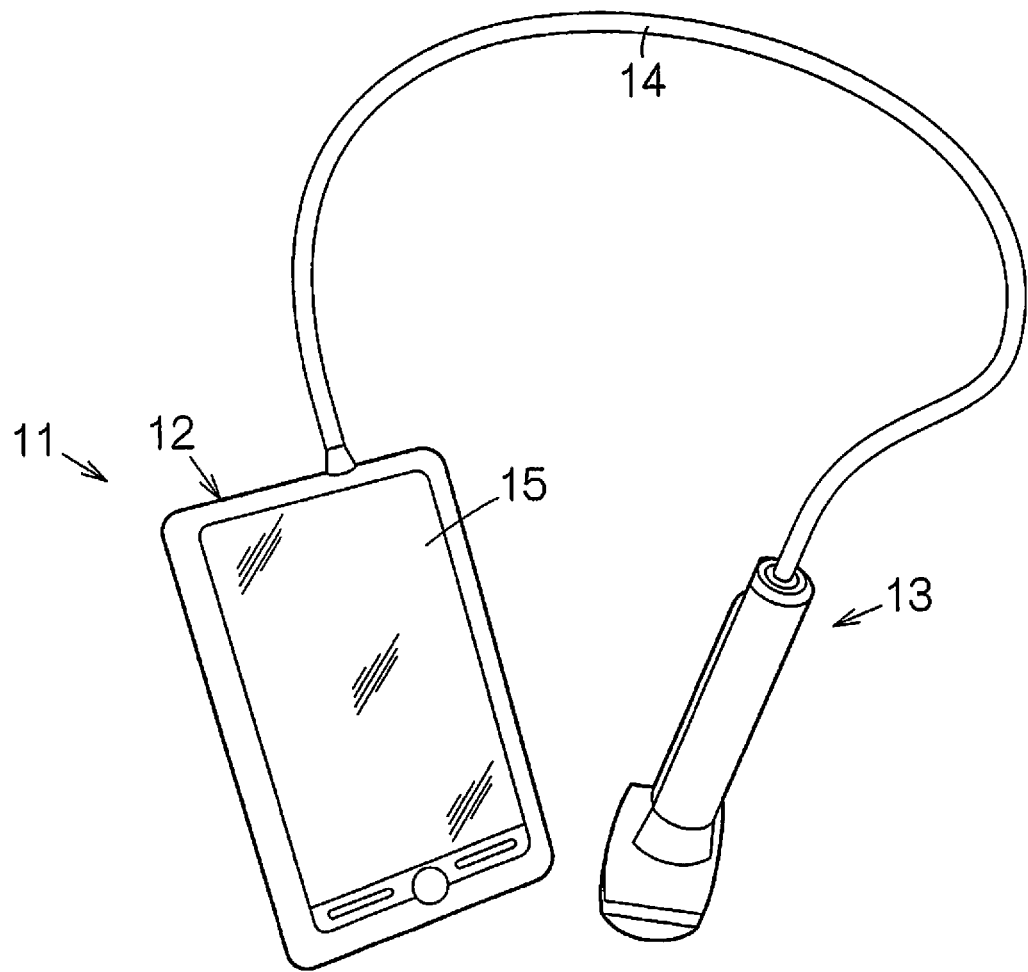
FIG. 1 is an external view schematically showing an example of an electronic instrument, that is, an ultrasonic diagnostic device according to one embodiment.

FIG. 1 schematically shows a configuration of an ultrasonic diagnostic device (ultrasonic image device) 11 as an example of an electronic instrument according to an embodiment of the present invention. The ultrasonic diagnostic device 11 is provided with a device terminal 12 and an ultrasonic probe (probe) 13. The device terminal 12 and the ultrasonic probe 13 are connected to each other through a cable 14. The device terminal 12 and the ultrasonic probe 13 exchange electric signals through the cable 14. A display panel (display device) 15 is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
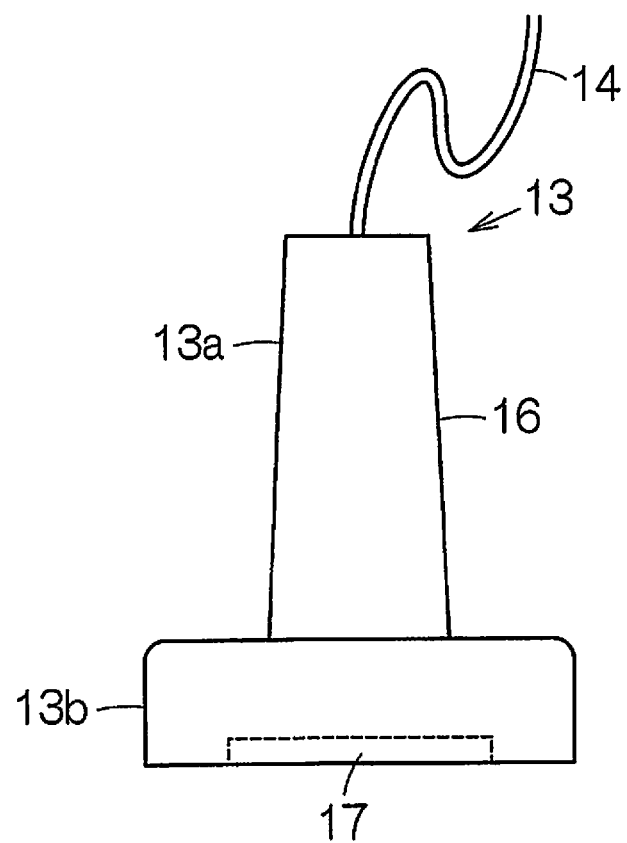
FIG. 2 is an enlarged front view of an ultrasonic probe.

As shown in FIG. 2, the ultrasonic probe 13 has a case 16. An ultrasonic transducer element unit (hereinafter referred to as "element unit") 17 is housed in the case 16. The ultrasonic transducer element unit 17 is a specific example of an ultrasonic transducer device, according to an embodiment of the present invention. A surface of the element unit 17 may be exposed on a surface of the case 16. The element unit 17 outputs ultrasonic waves from the surface thereof, and receives reflected waves of ultrasonic waves. In addition, the ultrasonic probe 13 can be equipped with a probe head 13b linked to be freely attachable and detachable with the probe main unit 13a. At this time, the element unit 17 can be incorporated inside the case 16 of the probe head 13b.

Figure 3:
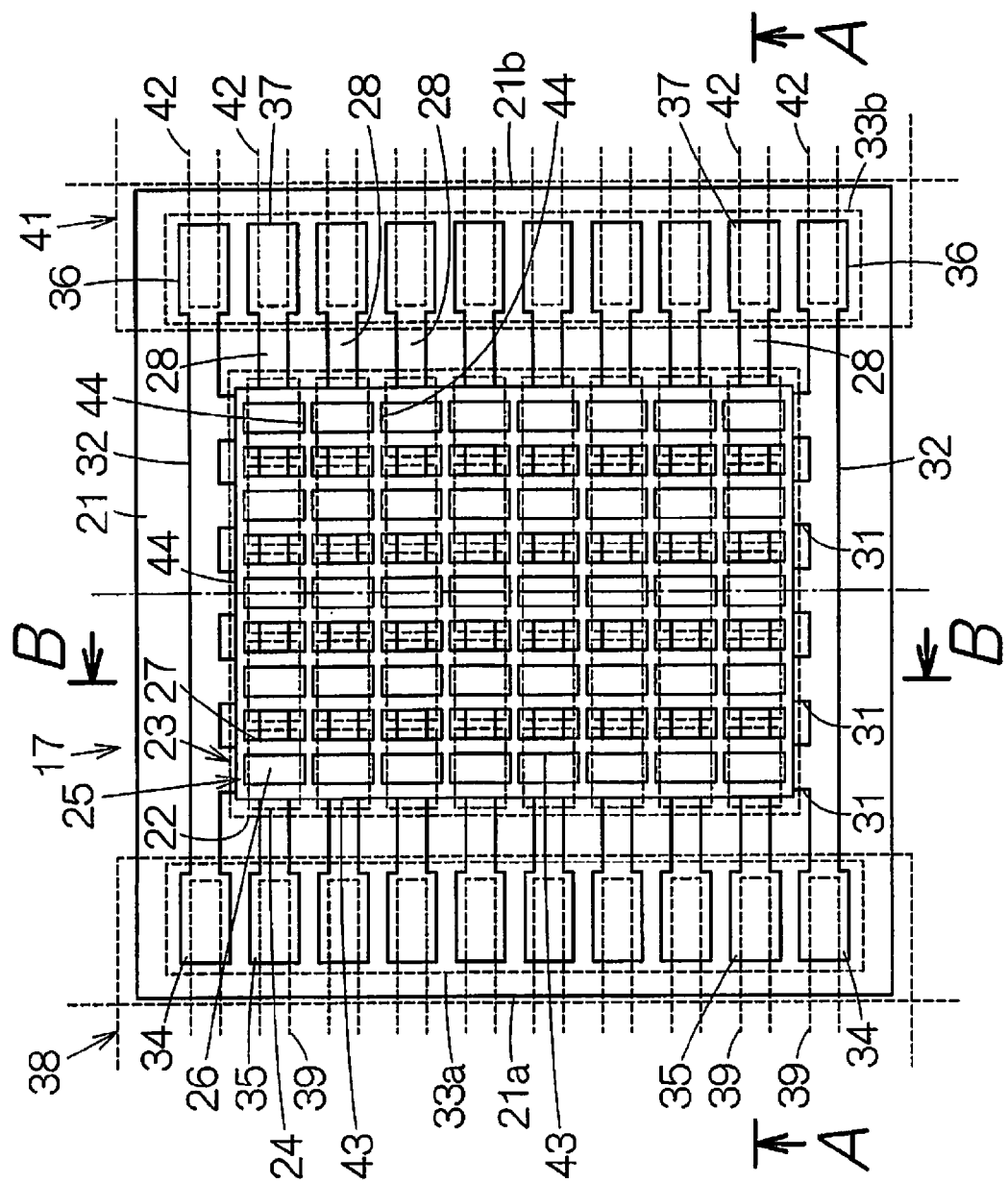
FIG. 3 is an enlarged plan view of an ultrasonic transducer element unit according to the first embodiment.

FIG. 3 schematically shows a plan view of the element unit 17 according to the first embodiment. The element unit 17 is provided with a base 21. An element array 22 is formed on the base 21. The element array 22 is constructed of ultrasonic transducer elements (hereinafter referred to as "element") 23 arranged in an array pattern. The array is formed in a matrix having a plurality of rows and a plurality of columns. In addition, a zigzag pattern may be used in the array. In the zigzag pattern, a group of the elements 23 in an even column may be displaced with respect to a group of the elements 23 in an odd column by one-half of the row pitch. The number of the elements in one of an odd column and an even column may be smaller than the number of the elements in the other of an odd column and an even column by one.

Each element 23 is equipped with a vibrating film 24 (one example of a vibrating film portion). Details of the vibrating film 24 are described later. In FIG. 3, the outline of the vibrating film 24 is depicted with a dotted line with a plan view in the direction orthogonal to the film surface of the vibrating film 24 (plan view in the substrate thickness direction). The inside of the outline correlates to the area interior of the vibrating film 24. The outside of the outline correlates to the area exterior of the vibrating film 24. A piezoelectric element 25 is formed on the vibrating film 24. As described later, with the piezoelectric element 25, a piezoelectric film (not illustrated) is sandwiched between an upper electrode (second electrode) 26 and a lower electrode (first electrode) 27. These are layered in sequence. The element unit 17 is constituted as one ultrasonic transducer element chip.

A plurality of first conductive bodies 28 are formed on the surface of the base 21. The first conductive bodies 28 extend parallel to each other in the column direction of the array. One conductive body 28 is allocated for each element 23 of one column. One first conductive body 28 is arranged in common with elements 23 aligned in the column direction of the array. The first conductive bodies 28 form the lower electrode 27 for each of the elements 23. The first conductive bodies 28 form the conductive body connected to the lower electrode 27, specifically, the first conductive body part. In this way, the first conductive bodies 28 are arranged in the vibrating film 24 area interior and area exterior. For the first conductive body 28, it is possible to use a layered film of titanium (Ti), iridium (Ir), platinum (Pt), and titanium (Ti), for example. However, it is also possible to use other conductive materials for the first conductive body 28.

A plurality of second conductive bodies 31 are formed on the surface of the base 21. The second conductive bodies 31 extend parallel to each other in the row direction of the array. One second conductive body 31 is allocated to each element 23 of one row. The one second conductive body 31 is connected in common to the elements 23 aligned in the row direction of the array. The second conductive bodies 31 form the upper electrode 26 for each of the elements 23. The second conductive bodies 31 form the conductive body connected to the upper electrode 26, specifically, the second conductive body part. Both ends of the second conductive body 31 are respectively connected to a pair of extraction wirings 32. The extraction wirings 32 extend parallel to each other in the column direction of the array. Therefore, all of the second conductive bodies 31 have the same length. In this way, the upper electrodes 26 are connected in common to the elements 23 of the entire matrix. In this way, the second conductive bodies 31 are arranged in the vibrating film 24 inside area and outside area. The second conductive body 31 can be formed using iridium (Ir), for example. However, it is also possible to use other conductive materials for the first conductive body 28.

Power distribution of the elements 23 is switched per column. Linear scanning or sector scanning is achieved corresponding to such switching of power distribution. Since the elements 23 in one column output ultrasonic waves at the same time, the number of the elements 23 in one column, that is, the number of rows of the array can be determined based on the output level of ultrasonic waves. For example, the number of rows may be set to be around 10 to 15 rows. In the drawing, five rows are illustrated for simplicity. The number of columns of the array can be determined based on the extent of an area to be scanned. For example, the number of columns may be set to be 128 columns or 256 columns. In the drawing, eight columns are illustrated for simplicity. The role of the upper electrode 26 and the lower electrode 27 can also be switched. Specifically, while the lower electrode is connected in common to the elements 23 of the entire matrix, the upper electrode can be connected in common for each column of the array.

The outline of the base 21 has a first side 21a and a second side 21b that are opposed and partitioned by a pair of straight lines in parallel to each other. One line of a first terminal array 33a is arranged between the first side 21a and the outline of the element array 22. One line of a second terminal array 33b is arranged between the second side 21b and the outline of the element array 22. For the first terminal array 33a, one line can be formed in parallel to the first side 21a. For the second terminal array 33b, one line can be formed in parallel to the second side 21b. The first terminal array 33a is constructed of a pair of upper electrode terminals 34 and a plurality of lower electrode terminals 35. Similarly, the second terminal array 33b is constructed of a pair of upper electrode terminals 36 and a plurality of lower electrode terminals 37. Upper electrode terminals 34 and 36 are respectively connected to both ends of one extraction wiring 32. It is sufficient for the extraction wirings 32 and the upper electrode terminals 34 and 36 to be formed plane-symmetrically with respect to a vertical plane that bisects the element array 22. Lower electrode terminals 35 and 37 are respectively connected to both ends of one second conductive body 31. It is sufficient for the second conductive bodies 31 and the lower electrode terminals 35 and 37 to be formed plane-symmetrically with respect to the vertical plane that bisects the element array 22. The outline of the base 21 is formed to be a rectangle. The outline of the base 21 may be a square or a trapezoid.

A first flexible printed wiring board (hereinafter referred to as "first wiring board") 38 is coupled to the base 21. The first wiring board 38 covers the first terminal array 33a. Conductive lines, that is, first signal lines 39 are formed at one end of the first wiring board 38 corresponding to the upper electrode terminals 34 and the lower electrode terminals 35, respectively. The first signal lines 39 are respectively opposed to the upper electrode terminals 34 and the lower electrode terminals 35, and respectively bonded thereto. Similarly, a second flexible printed wiring board (hereinafter referred to as "second wiring board") 41 covers the base 21. The second flex 41 covers the second terminal array 32b. Conductive lines, that is, second signal lines 42 are formed at one end of the second wiring board 41 corresponding to the upper electrode terminals 36 and the lower electrode terminals 37, respectively. The second signal lines 42 are respectively opposed to the upper electrode terminals 36 and the lower electrode terminals 37, and respectively bonded thereto.

An electrode separation film (fourth insulating film) 43 is arranged in parallel to the second conductive body 31 on the vibrating film 24. The electrode separation film 43 extends in band form in the lengthwise direction of the second conductive body 31. The electrode separation film 43 has insulation properties and moisture proof properties. The electrode separation film 43 is formed from a moisture proof insulating material such as alumina ($Al_2O_3$), silicon oxide ($SiO_2$) or the like, for example. The electrode separation films 43 are formed sandwiching each second conductive body 31 and separated at both sides of the second conductive body 31. The second conductive body 31 intersects the first conductive body 28 on the vibrating film 24, so the electrode separation film 43 crosses over the first conductive body 28 on the vibrating film 24.

An insulating film 44 is formed at the vibrating film 24 area exterior on the base 21. The insulating film 44 extends in band form in the lengthwise direction of the first conductive body 28. The insulating film 44 is arranged in parallel with the first conductive body 28 only at the vibrating film 24 area exterior. The insulating film 44 is formed from an insulating material with moisture proof properties such as alumina or silicon oxide, for example. The material of the insulating film 44 is sufficient as long as it matches the material of the electrode separation film 43. The insulating film 44 crosses over the second conductive body 31. In this way, the insulating film 44 is formed on the second conductive body 31. The insulating film 44 is continuous with the electrode separation film. The insulating film 44 is connected to the electrode separation film 43 sandwiching the second conductive body 31 and arranged at both sides of the second conductive body 31.

Figure 4:
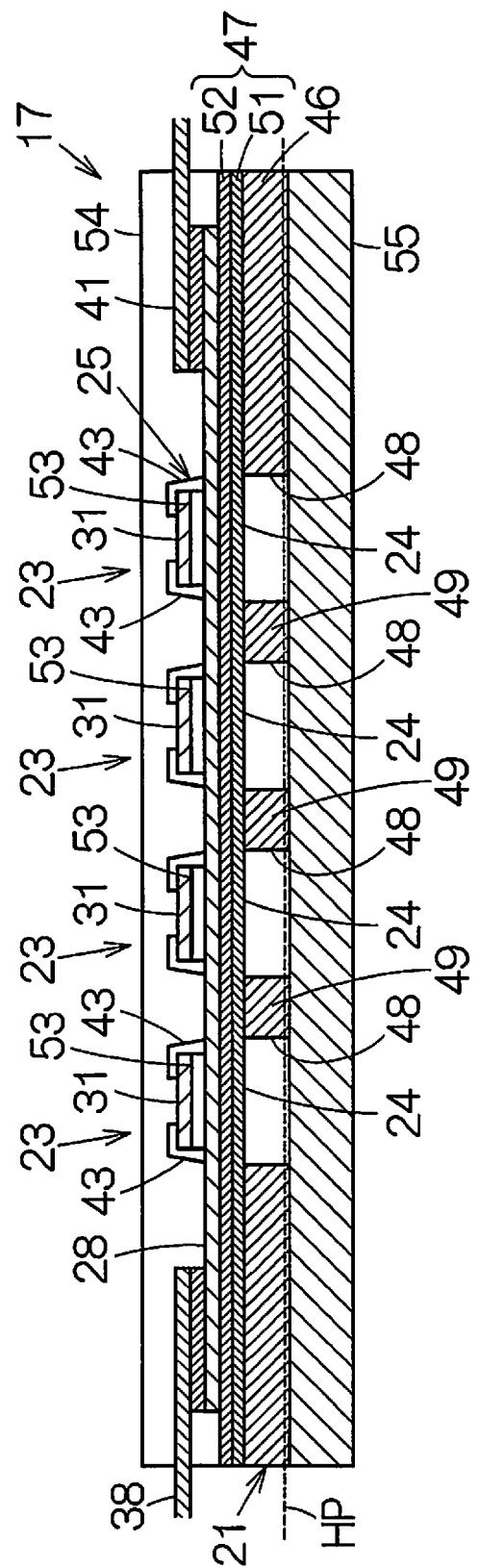
FIG. 4 is a schematic cross section view along line A-A of FIG. 3.

As shown in FIG. 4, the base 21 is equipped with a substrate 46 and a flexible film 47. The flexible film 47 is formed on the entire surface on the surface of the substrate 46. An opening 48 is formed in each of the elements 23 on the substrate 46. The openings 48 are arranged in an array pattern on the substrate 46. The outline of the area in which the openings 48 are arranged correlates to the outline of the element array 22. A partition wall 49 divides between two adjacent openings 48. The adjacent openings 48 are partitioned by, the partition wall 49. The wall thickness of the partition wall 49 correlates to the gap of the openings 48. The partition wall 49 defines two wall surfaces on the inside of the plane that expand parallel to each other. The wall thickness correlates to the distance between the two wall surfaces. Specifically, the wall thickness can be defined as the length of the vertical line orthogonal to the wall surface and sandwiched between the wall surfaces.

The flexible film 47 is constructed of a silicon oxide ($SiO_2$) layer 51 layered on the surface of the substrate 46, and a zirconium oxide ($ZrO_2$) layer 52 layered on a surface of the silicon oxide layer 51. The flexible film 47 contacts the openings 48. In this manner, a part of the flexible film 47 corresponding to the outline of the opening 48 forms the vibrating film 24. Of the flexible film 47, the vibrating film 24 is the part that is able to do film vibration in the thickness direction of the substrate 46 since it opposes the opening 48. The film thickness of the silicon oxide layer 51 can be determined based on the resonance frequency.

The first conductive body 28, the piezoelectric film 53, and the second conductive body 31 are layered on a surface of the vibrating film 24 in this order. The piezoelectric film 53 may be formed of piezoelectric zirconate titanate (PZT), for example. Another piezoelectric material may be used for the piezoelectric film 53. The piezoelectric film 53 covers at least a portion of the lower electrode 27 and a portion of the vibrating film 24. The upper electrode 26 covers at least a portion of the piezoelectric film 53. Here, the piezoelectric film 53 completely covers the surface of the first conductive body 28 under the second conductive body 31. The function of the piezoelectric film 53 is to prevent a short circuit between first conductive body 28 and the second conductive body 31.

As shown in FIG. 4, the electrode separation film 43 covers the side surface of the piezoelectric element 25. Specifically, the electrode separation film 43 is formed on the piezoelectric film 53 between the first conductive body 28 and the second conductive body 31. In this way, the surface of the piezoelectric film 53 is covered by the electrode separation film 43 between the first conductive body 28 and the second conductive body 31. Here, the electrode separation film 43 stays inside the area of the vibrating film 24 in the lengthwise direction of the first conductive body 28. The electrode separation film 43 does not affect the edge of the vibrating film 24.

A protective film 54 is layered on the surface of the base 21. The protective film 54 covers the surface of the base 21 across the entire surface, for example. As a result, the element array 22, the first and second terminal arrays 33a and 33b, and the first and second wiring boards 38 and 41 are covered by the protective film 54. For the protective film 54, for example, a silicone resin film can be used. The protective film 54 protects the structure of the element array 22, the bonding of the first terminal array 33a and the first wiring board 38, and the bonding of the second terminal array 33b and the second wiring board 41.

A reinforcing plate 55 is fixed to a reverse surface of the base 21. The reverse surface of the base 21 is overlapped on a surface of the reinforcing plate 55. The reinforcing plate 55 closes the openings 48 in the reverse surface of the element unit 17. The reinforcing plate 55 may have a rigid base material. For example, the reinforcing plate 55 may be formed of a silicon base plate. The plate thickness of the base 21 is set to be around 100 µm, for example, and the plate thickness of the reinforcing plate 55 is set to be around 100 to 150 µm, for example. The partition walls 49 are bonded to the reinforcing plate 55. The reinforcing plate 55 is bonded to each partition wall 49 in at least one bonding area location. For bonding, an adhesive agent can be used.

Figure 5:
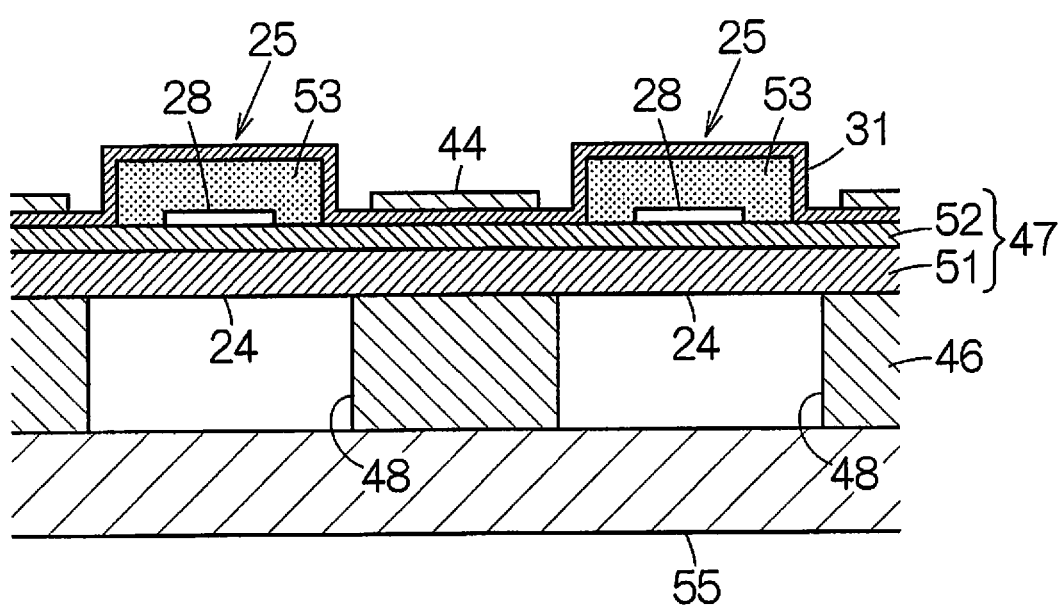
FIG. 5 is a schematic cross section view along line B-B of FIG. 3.

As shown in FIG. 5, the piezoelectric film 53 is covered by the first conductive body 28. The piezoelectric film 53 contacts the surface of the vibrating film 24 in a range expanding from the edge of the first conductive body 28 to the outside. The piezoelectric film 53 completely separates the first conductive body 29 and the second conductive body 31 from each other. Short circuits between the first conductive body 28 and the second conductive body 31 are avoided. In this way, it is possible for the second conductive body 31 to extend in the array row direction without interruption. The insulating film 44 covers the second conductive body 31. The insulating film 44 ends at the vibrating film 24 area exterior. The insulating film 44 stays at the vibrating film 24 area exterior and does not enter the area interior.

(2) Circuit Configuration of Ultrasonic Diagnostic Device

Figure 6:
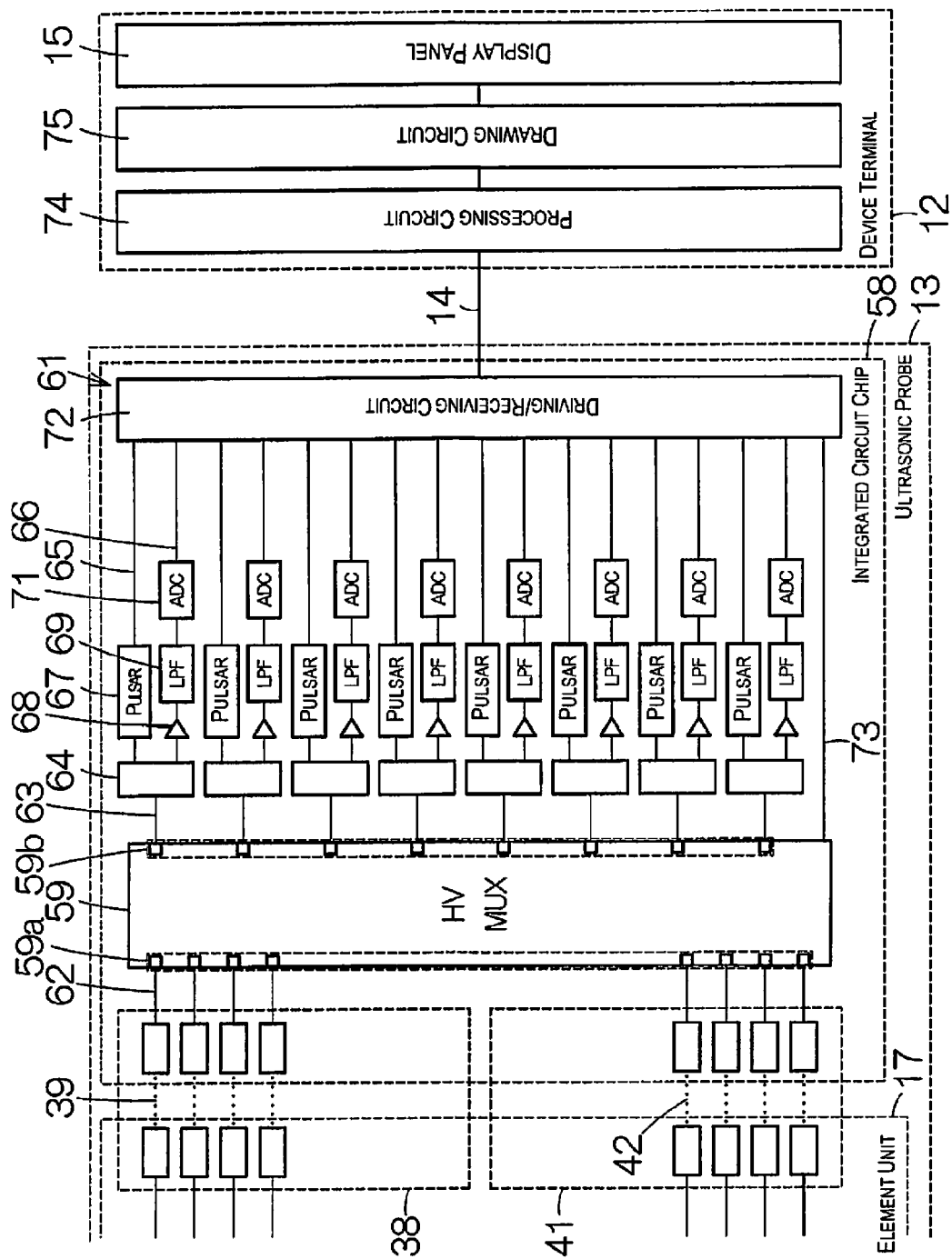
FIG. 6 is a block diagram schematically showing the circuit configuration of the ultrasonic diagnostic device.

As shown in FIG. 6, the ultrasonic diagnostic device 11 is equipped with an integrated circuit chip 58 electrically connected to the element unit 17. The integrated circuit chip 58 is equipped with a multiplexer 59 and a transmitting and receiving circuit 61. The multiplexer 59 has a group of ports 59a on the element unit 17 side, and a group of ports 59b on the transmitting and receiving circuit 61 side. The first signal lines 39 and the second signal lines 42 are connected to the group of ports 59a on the element unit 17 side via the wiring 62. In this manner, the group of ports 59a is connected to the element array 22. Here, a prescribed number of signal lines 63 within the integrated circuit chip 55 are connected to the group of ports 59b on the transmitting and receiving circuit 61 side. The prescribed number corresponds to a column number of the elements 23 output at the same time as scanning is conducted. The multiplexer 59 controls interconnection between the ports on the cable 14 side and the ports on the element unit 17 side.

The transmitting and receiving circuit 61 has a prescribed number of changing switches 64. The changing switches 64 are connected to the corresponding signal lines 63, respectively. The transmitting and receiving circuit 61 has a transmission channel 65 and a reception channel 66 for each of the changing switches 64. The transmission channel 65 and the reception channel 66 are connected to the changing switch 64 in parallel. The changing switch 64 selectively connects the transmission channel 65 or the reception channel 66 to the multiplexer 59. Pulsars 67 are incorporated in the transmission channel 65. The pulsars 67 output a pulse signal at a frequency corresponding to the resonance frequency of the vibrating film 24. An amplifier 68, a low-pass filter (LPF) 69, and an analog-digital converter (ADC) 71 are incorporated in the reception channel 66. The output signal of each of the elements 23 is amplified, and converted into a digital signal.

The transmitting and receiving circuit 61 has a driving/receiving circuit 72. The transmission channel 65 and the reception channel 66 are connected to the driving/receiving circuit 72. The driving/receiving circuit 72 controls the pulsars 67 simultaneously depending on the state of scanning. The driving/receiving circuit 72 receives a digital signal of an output signal depending on the state of scanning. The driving/receiving circuit 72 is connected to the multiplexer 59 through a control line 73. The multiplexer 59 conducts control of interconnection based on a control signal supplied from the driving/receiving circuit 72.

A processing circuit 74 is incorporated in the device terminal 12. The processing circuit 74 can be provided with a central processing unit (CPU) and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with an output signal of the element 23. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in accordance with drawing data generated in the processing circuit 74. The driving signal is sent to the display panel 15. As a result, an image is displayed on the display panel 15.

(3) Operation of Ultrasonic Diagnostic Device

Next, the operation of the ultrasonic diagnostic device 11 will be explained briefly. The processing circuit 74 switches between an ultrasonic diagnostic mode and a sensitivity detection mode. In the ultrasonic diagnostic mode, ultrasonic diagnosis can be implemented using the ultrasonic diagnostic device 11. In the sensitivity detection mode, it is possible to determine a decrease in the sensitivity of the piezoelectric element part 24. When the processing circuit 74 selects the ultrasonic diagnostic mode, the processing circuit gives the driving/receiving circuit 72 instructions to transmit and receive ultrasonic waves. The driving/receiving circuit 72 supplies a control signal to the multiplexer 59, and supplies a driving signal to each of the pulsars 67. The pulsars 67 output pulse signals in response to the supply of the driving signal. The multiplexer 59 connects the port of the group of ports 59a to the port of the group of ports 59b in response to the instructions of the control signal. The pulse signals are supplied to the elements 23 per column through the upper electrode terminals 34 and 36 and the lower electrode terminals 35 and 37 according to the selection of the port. The vibrating film 24 vibrates in response to the supply of the pulse signals. As a result, desired ultrasonic wave beams are emitted toward a target (for example, the inside of a human body).

After ultrasonic waves are transmitted, the changing switch 64 is switched. The multiplexer 59 maintains the connection relation of the ports. The changing switch 64 establishes a connection between the reception channel 66 and the signal line 63 instead of a connection between the transmission channel 65 and the signal line 63. Reflected waves of ultrasonic waves vibrate the vibrating film 24. As a result, an output signal is output from the element 23. The output signal is converted into a digital signal, and sent to the driving/receiving circuit 72.

Transmission and reception of ultrasonic waves are repeated. For this repetition, the multiplexer 59 changes the connection relation of the ports. As a result, linear scanning or sector scanning is achieved. When scanning is finished, the processing circuit 74 generates an image based on the digital signals of the output signals. The generated image is displayed on the screen of the display panel 15.

The ultrasonic waves act on the vibrating film 24. The ultrasonic waves cause ultrasonic vibration of the vibrating film 24. Current is output from the piezoelectric element 25 according to the ultrasonic vibration of the vibrating film 24. In this way, each element 23 detects ultrasonic waves. Here, the insulating film 44 protects the second conductive body 31. The insulating film 44 does not affect the vibrating film 24, so the flexibility of the vibrating film 24 is maintained well. Therefore, it is possible to maintain the ultrasonic wave detection sensitivity.

The electrode separation film 43 insulates the first conductive body 28 and the second conductive body 31 from each other. Short circuits are prevented between the first conductive body 28 and the second conductive body 31. The electrode separation film 43 is continuous with the insulating film 44, so the insulating film 44 is bonded to the conductive body 31, and increases the bonding strength of the electrode separation film 43. In particular, the insulating film 44 stipulates displacement in the mutually separating direction by the two electrode separation films 43 which sandwich the second conductive body and are arranged at both sides of the second conductive body 31, so for example even if the electrode separation film 43 is formed on the side wall of the piezoelectric element 25, it is possible to reliably increase the bonding strength of the electrode separation film 43. In addition, the insulating film 44 is formed on the surface of the base 21, so it is possible to increase the bonding strength of the insulating film 44. As a result, the bonding strength of the electrode separation film is increased.

With this embodiment, the electrode separation film 43 has moisture proof properties. The electrode separation film 43 is embedded between the first conductive body 28 and the second conductive body 31, so the electrode separation film 43 has a waterproofing function at the surface of the piezoelectric film 53. The electrode separation film 43 prevents the infiltration of moisture, and inhibits short circuits between the first conductive body 28 and the second conductive body 31.

(4) Element Unit According to Second Embodiment

Figure 7:
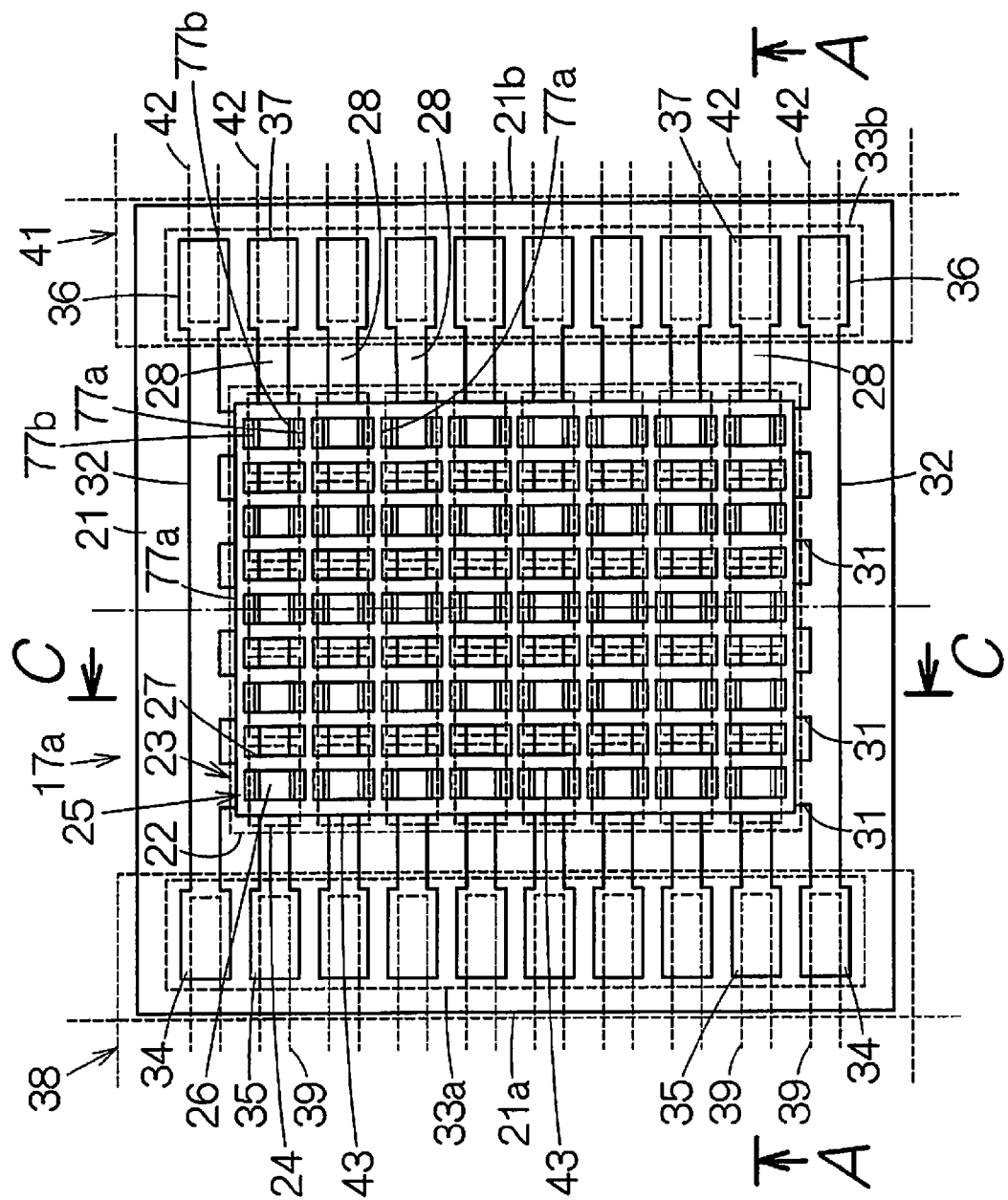
FIG. 7 is an enlarged plan view of an ultrasonic transducer element unit according the second embodiment.
Figure 8:
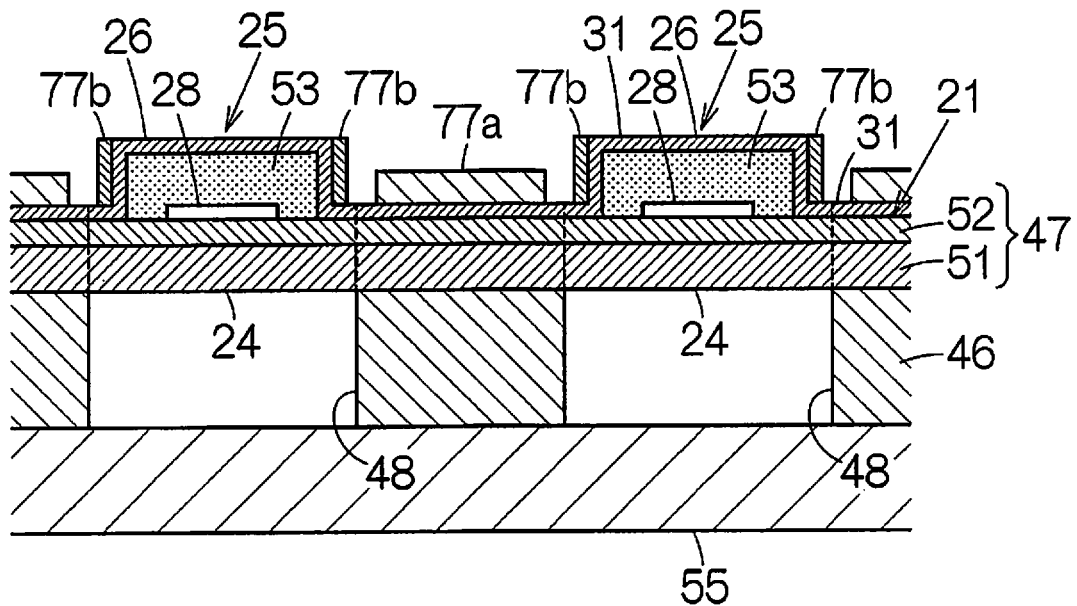
FIG. 8 is a schematic cross section view along line C-C of FIG. 7.

FIG. 7 schematically shows a plan view of the element unit 17a of the second embodiment. FIG. 8 is a schematic cross section view along line C-C of FIG. 7. The cross section view along line A-A of FIG. 7 is similar to that shown in FIG. 4, and thus, omitted herein. With this second embodiment, a first insulating film 77a is formed in the vibrating film 24 area exterior on the base 21. The first insulating film 77a extends in band form in the lengthwise direction of the first conductive body 28. The first insulating film 77a, similar to the previously described insulating film 44, is arranged in parallel with the first conductive body 29 only in the vibrating film 24 area exterior. The first insulating film 77a is formed for example from a moisture proof insulating material such as alumina or silicon oxide, for example. The material of the first insulating film 77a is sufficient as long as it matches the material of the electrode separation film 43. The first insulating film 77a crosses over the second conductive body 31. In this way, the first insulating film 77a is formed on the second conductive body 31. The first insulating film 77a is continuous with the electrode separation film 43. The first insulating film 77a is connected to the electrode separation film 43 sandwiching the second conductive body 31 and arranged at both sides of the second conductive body 31.

A second insulating film 77b is formed on the inside area of the vibrating film 24. The second insulating film 77b extends in band form in the lengthwise direction of the first conductive body 28. The second insulating film 77b extends in parallel to the first insulating film 77a between adjacent electrode separation films 43. The second insulating film 77b covers at least a portion of the piezoelectric element 25, and is arranged only on the area interior with a break with the vibrating film 24 area interior. The second insulating film 77b is formed from a moisture proof insulating material such as alumina or silicon oxide, for example. The material of the second insulating film 77b is sufficient as long as it matches the material of the electrode separation film 43. Here, as is clear from FIG. 8, the second insulating film 77b covers the side surface of the piezoelectric element 25. The second insulating film 77b is formed so as to cover the piezoelectric film 53 not covered by the second conductive body 31. The second insulating film 77b has a smaller film thickness than the film thickness of the first insulating film 77a. At this time, the film thickness of the second insulating film 77b is measured in the direction perpendicular to the side surface of the piezoelectric element 25. The second insulating film 77b is continuous with the electrode separation film 43. The second insulating film 77b is connected to the electrode separation film 43 sandwiching the second conductive body 31 and arranged at both sides of the second conductive body 31.

The first insulating film 77a and the second insulating film 77b protect the second conductive body 31. The first insulating film 77a does not affect the vibrating film 24, so the flexibility of the vibrating film 24 is maintained well. Therefore, it is possible to maintain the ultrasonic wave detection sensitivity. In addition, the second insulating film 77b protects the piezoelectric element 25. The second insulating film 77b does not cross over the edge of the vibrating film 24, so it is possible to maintain the vibrating film 24 vibration operation well. In fact, the second insulating film 77b is formed on the side wall of the piezoelectric element 25, so the effect on the flexibility of the vibrating film 24 is suppressed to a minimum. The flexibility of the vibrating film 24 can be maintained well. Furthermore, the second insulating film 77b stipulates that the electrode separation film 43 arranged sandwiching the second conductive body 31 be displaced in the direction separating from each other, so the bonding strength of the electrode separation film 43 is further increased.

Figure 9:
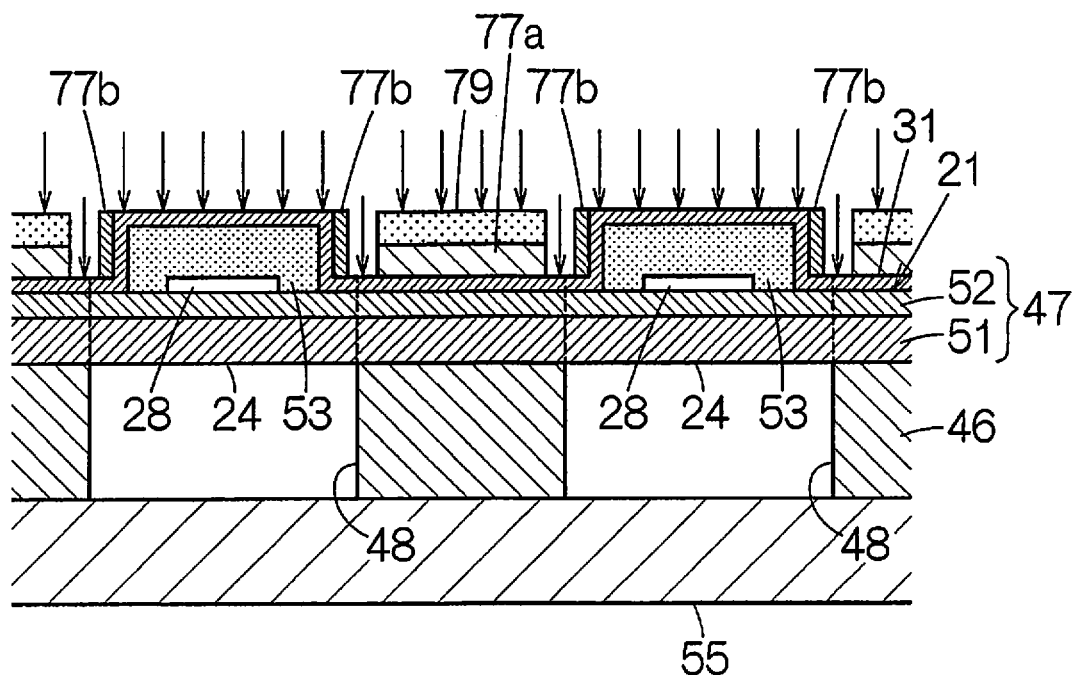
FIG. 9 is a schematic cross section view schematically showing the formation method of the first insulating film and the second insulating film corresponding to FIG. 8.

As shown in FIG. 9, for formation of the first insulating film 77a and the second insulating film 77b, an insulating material layer is formed uniformly on the entire surface on the surface of the base 21. For formation, it is possible to use sputtering, for example. A resist film 79 is formed on the insulating material layer. The resist film 79 is modeled on the shape of the first insulating film 77a. Here, for example when ion etching processing is implemented, the insulation material layer is removed in areas other than that of the resist film 79. At this time, the insulation material layer remains under the resist film 79. In the periphery of the resist film 79, removal of the insulation material layer at the wall surface of the piezoelectric element 25 is delayed compared to on the surface of the base 21, the surface of the vibrating film 24, and the top surface of the piezoelectric element 25. As a result, even if the insulation material layer is completely removed at the surface of the base 21 and the surface of the vibrating film 24 and the top surface of the piezoelectric element 25, the insulation material layer remains at the side wall of the piezoelectric element 25. In this way, the second insulating film 77b is formed. Compared to under the resist film 79, at the wall surface of the piezoelectric element 25, the insulation material layer is exposed by etching, so the film thickness of the second insulating film 77b is reduced more than the film thickness of the first insulating film 77a.

Figure 10:
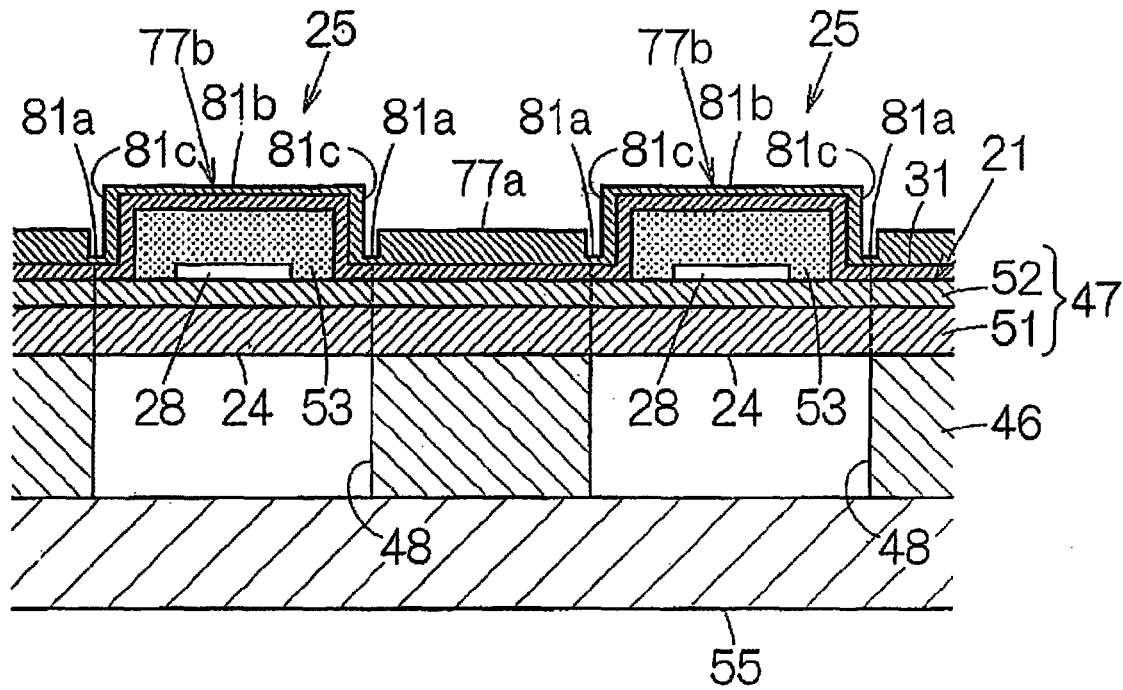
FIG. 10 is a schematic cross section view of the ultrasonic transducer element unit according to a modification example of the second embodiment corresponding to FIG. 8.

As shown in FIG. 10, it is also possible to further form a third insulating film 81a on the base 21. The third insulating film 81a connects the second insulating film 77b to the first insulating film 77a. The second insulating film 77b has a first film body part 81b and a second film body part 81c. The first film body part 81b is arranged on the top surface of the piezoelectric element 25. The second film body part 81c covers the second conductive body 31 formed on the piezoelectric film 53 at the side wall of the piezoelectric element 25. The first film body part 81b connects adjacent second film body parts 81c to each other. The third insulating film 81a and the second insulating film 77b are formed from a moisture proof insulating material such as alumina or silicon oxide, for example. The material of the first insulating film 77a is sufficient as long as it matches the material of the electrode separation film (fourth insulating film) 43. It is sufficient to have the third insulating film 81a and the first film body part 81b film thickness match. The film thickness of the third insulating film 81a and the first film body part 81b is smaller than the film thickness of the second film body part 81c. The third insulating film 81a, the first film body part 81b and the second film body part 81c are continuous with the electrode separation film (fourth insulating film) 43 sandwiching the second conductive body 31 and arranged at both sides of the second conductive body 31.

The third insulating film 81a and the first film body part 81b are covered on the second conductive body 31 on the inside area of the vibrating film 24. The third insulating film 81a and the first film body part 81b protect the second conductive body 31. At this time, the third insulating film 81a is thinner than the first insulating film 77a and the second insulating film 77b, so it is possible to maintain the vibrating operation of the vibrating film 24 well. In fact, the third insulating film 81a and the first film body part 81b stipulate that the electrode separation film 43 arranged sandwiching the second conductive body 31 be displaced in the direction separating from each other, so the bonding strength of the electrode separation film 43 is further increased.

As described previously, for formation of the first insulating film 77a and the second insulating film 77b, it is possible to use ion etching processing. At this time, if the insulating material layer remains on the surface of the base 21, the surface of the vibrating film 24, and the wall surface and the top surface of the piezoelectric element 25, it is possible to form the third insulating film 81a and the first film body part 81b. In the periphery of the resist film 79, removal of the insulation material layer at the wall surface of the piezoelectric element 25 is delayed compared to on the surface of the base 21, the surface of the vibrating film 24, and the top surface of the piezoelectric element 25, so the film thickness of the third insulating film 81a and the first film body part 81b is reduced more than the film thickness of the second film body part 81c.

Figure 11:
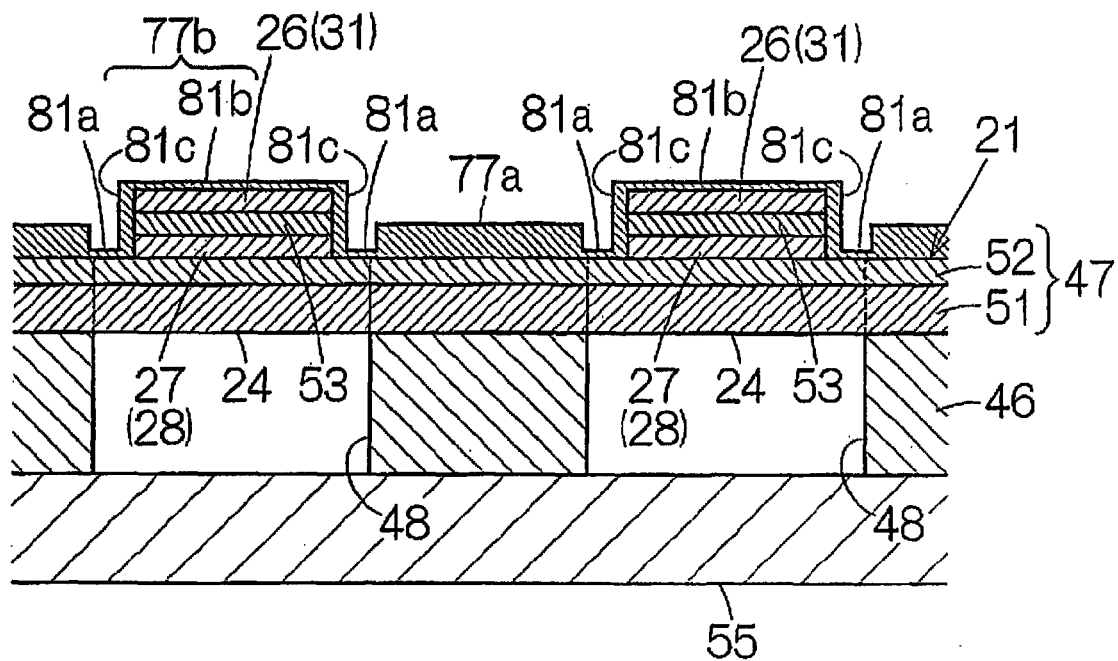
FIG. 11 is a schematic cross section view of the ultrasonic transducer element unit according to another modification example of the second embodiment corresponding to FIG. 8.

As shown in FIG. 11, with the piezoelectric element 25, it is also possible to layer the lower electrode 27, the piezoelectric film 53, and the upper electrode 26 in that sequence. In this case, the piezoelectric film 53 is separated from the surface of the vibrating film 24 by the lower electrode 27. The upper electrode 26 is separated from the lower electrode 27 by the piezoelectric film 53. The lower electrode 27, the piezoelectric film 53, and the upper electrode 26 are exposed at the side surface of the piezoelectric element 25. The second film body part 81c of the second insulating film 77b covers the upper electrode 26, the piezoelectric film 53, and the lower electrode 27 at the side surface of the piezoelectric element 25. The second insulating film 77b insulates the upper electrode 26 and the lower electrode 27. The second insulating film 77b prevents short circuits between the upper electrode 26 and the lower electrode 27. The first film body parts 81b of the second insulating film 77b covers the second conductive body 31 at the top surface of the piezoelectric element 25. The second conductive body 31 can reliably be protected. With the embodiment shown in FIG. 11, the same as described previously, the first insulating film 77a and the second film body part 81c of the second insulating film 77b can remain, and the third insulating film 81a and the first film body part 81b of the second insulating film 77b can be omitted.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the ultrasonic diagnostic device 11, the ultrasonic probe 13, the probe head 13b, the element units 17 and 17a, the elements 23 and the like are not limited to the present embodiment, and various changes and modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer device comprising:
    a base having a plurality of vibrating film portions arranged in an array pattern;
    a plurality of piezoelectric elements respectively disposed on the vibrating film portions;
    a conductive body disposed on the base, and arranged inside and outside of an area corresponding to each of the vibrating film portions in a plan view as viewed along a thickness direction of the base;
    a first insulating film disposed on the conductive body only at outside of the area corresponding to each of the vibrating film portions in the plan view; and
    a second insulating film having a film thickness smaller than a film thickness of the first insulating film, and disposed at least partially on each of the piezoelectric elements and only at inside of the area corresponding to each of the vibrating film portions in the plan view.

2. The ultrasonic transducer device according to claim 1, further comprising
    a third insulating film having a film thickness smaller than the film thickness of the second insulating film, and connected to the first insulating film and the second insulating film.

3. The ultrasonic transducer device according to claim 1, wherein
    each of the piezoelectric elements includes
        a first electrode disposed on the vibrating film portion,
        a piezoelectric film covering at least a portion of the first electrode, and
        a second electrode covering at least a portion of the piezoelectric film, and
    the conductive body includes
        a first conductive body part connected to the first electrode of each of the piezoelectric elements, and
        a second conductive body part connected to the second electrode of each of the piezoelectric elements; and
    the ultrasonic transducer device further comprises a fourth insulating film covering a portion of the piezoelectric film that is not covered by the second electrode or the second conductive body part.

4. The ultrasonic transducer device according to claim 3, wherein
the fourth insulating film includes two sections that sandwich the second electrode from both sides of the second electrode.

5. The ultrasonic transducer device according to claim 3, wherein
the piezoelectric film covers at least a portion of the first electrode and a portion of a corresponding one of the vibrating film portions, and
the second insulating film has a first film body part disposed on the second electrode and having a first film thickness, and a second film body part covering the piezoelectric film on side surfaces of the piezoelectric element and having a second film thickness greater than the first film thickness.

6. The ultrasonic transducer device according to claim 3, wherein
the piezoelectric film is layered on the first electrode, and separated from a surface of a corresponding one of the vibrating film portions by the first electrode,
the second electrode is layered on the piezoelectric film, and separated from the first electrode by the piezoelectric film, and
the second insulating film has a first film body part disposed on the second electrode and having a first film thickness, and a second film body part covering the second electrode, the piezoelectric film, and the first electrode on side surfaces of the piezoelectric element and having a second film thickness greater than the first film thickness.

7. A probe comprising:
the ultrasonic transducer device according to claim 1; and
a case supporting the ultrasonic transducer device.

8. An electronic instrument comprising:
the ultrasonic transducer device according to claim 1; and
a processing unit connected to the ultrasonic transducer device, and configured to process output signals from the ultrasonic transducer device.

9. An ultrasonic image device comprising:
the ultrasonic transducer device according to claim 1;
a processing unit connected to the ultrasonic transducer device, and configured to process output signals from the ultrasonic transducer device and generate an image; and
a display device configured to display the image.

10. An ultrasonic transducer device comprising:
a base having a plurality of openings and a plurality of vibrating film portions arranged in an array pattern, the plurality of the vibrating film portions being respectively disposed on the openings at inside of an area corresponding to each of the openings in a plan view as viewed along a thickness direction of the base, each of the openings having a rectangular shape defined by a pair of long sides and a pair of short sides in the plan view;
a plurality of piezoelectric elements respectively disposed on the vibrating film portions;
a conductive body disposed on the base, and arranged inside and outside of an area corresponding to each of the vibrating film portions in the plan view; and
an insulating film covering outside of the area corresponding to each of the vibrating film portions and only a portion of each of the long sides of the openings in the plan view.

11. The ultrasonic transducer device according to claim 10, wherein
the insulating film covers each of the short sides of the vibrating film portions in the plan view.

12. The ultrasonic transducer device according to claim 10, wherein
each of the piezoelectric elements includes
a first electrode disposed on the vibrating film portion,
a piezoelectric film covering at least a portion of the first electrode, and
a second electrode covering at least a portion of the piezoelectric film, and
the conductive body includes
a first conductive body part connected to the first electrode of each of the piezoelectric elements, and
a second conductive body part connected to the second electrode of each of the piezoelectric elements,
the insulating film covers a portion of the piezoelectric film that is not covered by the second electrode or the second conductive body part.

13. The ultrasonic transducer device according to claim 12, wherein
the insulating film is arranged at both sides of the second electrode so as to sandwich the second electrode.

14. A probe comprising:
the ultrasonic transducer device according to claim 10; and
a case supporting the ultrasonic transducer device.

15. An electronic instrument comprising:
the ultrasonic transducer device according to claim 10; and
a processing unit connected to the ultrasonic transducer device, and configured to process output signals from the ultrasonic transducer device.

16. An ultrasonic image device comprising:
the ultrasonic transducer device according to claim 10;
a processing unit connected to the ultrasonic transducer device, and configured to process output signals from the ultrasonic transducer device and generate an image; and
a display device configured to display the image.

17. An ultrasonic transducer device comprising:
a base having a plurality of vibrating film portions arranged in an array pattern;
a plurality of piezoelectric elements respectively disposed on the vibrating film portions;
a conductive body disposed on the base, and arranged inside and outside of an area corresponding to each of the vibrating film portions in a plan view as viewed along a thickness direction of the base, the conductive body covering an upper surface of each of the piezoelectric elements; and
an insulating film disposed on an upper surface of the conductive body at outside of the area corresponding to each of the vibrating film portions in the plan view.

18. A probe comprising:
the ultrasonic transducer device according to claim 17; and
a case supporting the ultrasonic transducer device.

19. An electronic instrument comprising:
the ultrasonic transducer device according to claim 17; and
a processing unit connected to the ultrasonic transducer device, and configured to process output signals from the ultrasonic transducer device.

20. An ultrasonic image device comprising:
the ultrasonic transducer device according to claim 17;

a processing unit connected to the ultrasonic transducer device, and configured to process output signals from the ultrasonic transducer device and generate an image; and a display device configured to display the image.

* * * * *